(12) United States Patent
Castellani et al.

(10) Patent No.: US 7,766,950 B2
(45) Date of Patent: Aug. 3, 2010

(54) HYPOTHERMIA TREATMENT SACK

(75) Inventors: Robert A. Castellani, Simpsonville, SC (US); Robert Miller, Simpsonville, SC (US)

(73) Assignee: North American Rescue, LLC, Greer, SC (US)

( * ) Notice: Subject to any disclaimer, the term of this patent is extended or adjusted under 35 U.S.C. 154(b) by 1047 days.

(21) Appl. No.: 11/491,338

(22) Filed: Jul. 21, 2006

(65) Prior Publication Data

US 2008/0021530 A1    Jan. 24, 2008

(51) Int. Cl.
*A61F 7/00* (2006.01)
(52) U.S. Cl. .................. 607/108; 607/112; 607/114
(58) Field of Classification Search .......... 607/108, 607/112, 114; 602/14
See application file for complete search history.

(56) References Cited

U.S. PATENT DOCUMENTS

| | | | | |
|---|---|---|---|---|
| 2,403,676 | A | * | 7/1946 | Modlinski ................ 2/94 |
| 2,649,584 | A | | 8/1953 | Chappell |
| 2,657,387 | A | | 11/1953 | Ketcham |
| 2,675,552 | A | | 4/1954 | Jackson |
| 2,683,262 | A | | 7/1954 | Foss |
| 2,931,043 | A | | 4/1960 | Achner |
| 3,096,759 | A | | 7/1963 | Coolbaugh |
| 3,228,034 | A | | 1/1966 | Grove |
| 3,443,066 | A | * | 5/1969 | Weibel ................ 219/527 |
| 3,610,251 | A | | 10/1971 | Sanderson |
| 3,695,507 | A | | 10/1972 | Sams |
| 3,708,810 | A | | 1/1973 | Merikallio |
| 3,714,947 | A | | 2/1973 | Hardy |
| 3,798,676 | A | | 3/1974 | Shanks et al. |
| 3,837,006 | A | | 9/1974 | Laseman |
| 3,999,037 | A | * | 12/1976 | Metcalf, Sr. ............ 219/211 |
| 4,030,646 | A | | 6/1977 | Switack et al. |
| 4,124,908 | A | | 11/1978 | Burns et al. |
| 4,186,453 | A | | 2/1980 | Burns et al. |
| 4,369,528 | A | * | 1/1983 | Vest et al. ................ 2/69 |
| 4,507,805 | A | | 4/1985 | Calutoiu |
| 4,734,072 | A | * | 3/1988 | Lastnik ................ 441/105 |
| 4,765,323 | A | * | 8/1988 | Poettgen ................ 128/849 |
| 4,867,230 | A | | 9/1989 | Voss |
| 4,922,562 | A | | 5/1990 | Allred et al. |
| 4,998,296 | A | | 3/1991 | Stames |
| 5,044,031 | A | | 9/1991 | Sherwood et al. |
| 5,046,204 | A | | 9/1991 | Mohler |
| 5,050,254 | A | | 9/1991 | Murphy |
| 5,121,514 | A | | 6/1992 | Rosane |

(Continued)

*Primary Examiner*—Roy D Gibson
*Assistant Examiner*—Kaitlyn E Helling
(74) *Attorney, Agent, or Firm*—McNair Law Firm, P.A.; Seann P. Lahey (57) ABSTRACT

A hypothermia treatment sack comprising a top sheet and a bottom sheet releasably connecting along their perimeters to form a patient receiving cavity between the top and bottom sheets while allowing for patient access from any location around the perimeter. The top and bottom sheets include a weatherproof exterior side for repelling wind and water, and a heat reflective interior side for preventing heat from escaping. A plurality of self-activating heating pads are carried in the top sheet for producing heat when exposed to air. The heating pads have a first side exposed on the weatherproof exterior side of the top sheet to provide for a generally unrestricted airflow to the heating pads, and a second side exposed on the heat reflective interior side of the top sheet for radiating heat directly into the patient receiving cavity.

37 Claims, 4 Drawing Sheets

U.S. PATENT DOCUMENTS

| | | | |
|---|---|---|---|
| 5,146,625 A * | 9/1992 | Steele et al. ................... 2/102 |
| 5,193,235 A | 3/1993 | Kircher |
| 5,230,645 A | 7/1993 | Cheng |
| 5,257,427 A | 11/1993 | Hinshaw |
| 5,300,101 A | 4/1994 | Augustine et al. |
| 5,363,663 A * | 11/1994 | Chen ............................ 62/99 |
| 5,383,918 A * | 1/1995 | Panetta ...................... 607/104 |
| D355,068 S | 2/1995 | Prendergast |
| 5,386,604 A | 2/1995 | Ricketts |
| 5,405,370 A | 4/1995 | Irani |
| 5,443,488 A | 8/1995 | Namenye et al. |
| 5,463,783 A * | 11/1995 | Pope ............................ 5/417 |
| 5,568,663 A | 10/1996 | Brown |
| 5,699,568 A | 12/1997 | Couldridge |
| 5,701,619 A | 12/1997 | Ullman |
| 5,722,094 A | 3/1998 | Ruefer |
| 5,735,890 A | 4/1998 | Kappel et al. |
| 5,737,785 A | 4/1998 | Casey |
| 5,749,109 A | 5/1998 | Kappel |
| 6,013,098 A | 1/2000 | Kappel et al. |
| 6,199,232 B1 | 3/2001 | Kocivar |
| 6,241,756 B1 | 6/2001 | Kappel |
| D458,711 S | 6/2002 | Kirkland |
| 6,409,745 B1 | 6/2002 | Ducharme et al. |
| 6,488,188 B2 * | 12/2002 | Fleischli .................... 224/153 |
| 6,743,250 B2 | 6/2004 | Renfro |
| 6,755,852 B2 * | 6/2004 | Lachenbruch et al. ....... 607/114 |
| 6,782,560 B1 | 8/2004 | Ascherl et al. |
| D504,753 S | 5/2005 | Gold et al. |
| 6,912,747 B2 | 7/2005 | DuPree et al. |
| 6,986,178 B2 | 1/2006 | Turner |
| 7,319,207 B2 * | 1/2008 | Campf et al. ............... 219/212 |
| 2002/0077681 A1 * | 6/2002 | Ducharme et al. .......... 607/108 |
| 2002/0157184 A1 | 10/2002 | Maturaporn |
| 2003/0061659 A1 | 4/2003 | Dunlap et al. |
| 2005/0044602 A1 | 3/2005 | Leach, II |
| 2005/0125047 A1 | 6/2005 | Gammons |
| 2005/0125048 A1 | 6/2005 | Paolini et al. |
| 2005/0143796 A1 | 6/2005 | Augustine et al. |
| 2006/0047332 A1 * | 3/2006 | Malmberg et al. .......... 607/104 |
| 2006/0069418 A1 | 3/2006 | Schock et al. .............. 607/104 |
| 2006/0247745 A1 * | 11/2006 | Thompson .................. 607/108 |
| 2006/0276089 A1 * | 12/2006 | Amarasinghe et al. ...... 442/121 |
| 2006/0282140 A1 * | 12/2006 | Schock et al. ............... 607/108 |
| 2007/0199148 A1 * | 8/2007 | Ricketts ......................... 5/627 |
| 2008/0021530 A1 * | 1/2008 | Castellani et al. ........... 607/108 |
| 2008/0027523 A1 * | 1/2008 | Behringer et al. ........... 607/109 |
| 2008/0147152 A1 * | 6/2008 | Quincy et al. ............... 607/112 |
| 2008/0201818 A1 * | 8/2008 | Nilforushan et al. ............. 2/69 |
| 2008/0209932 A1 * | 9/2008 | Clarke et al. ............... 62/259.3 |

* cited by examiner

HYPOTHERMIA TREATMENT SACK

BACKGROUND OF THE INVENTION

1) Field of the Invention

The present invention relates to a hypothermia prevention and management apparatus, and more particularly, to a hypothermia treatment sack for use in the field having a weatherproof exterior and a heat reflective interior that includes self-activating heating pads for heating the interior space of the sack to warm a patient placed therein.

2) Description of Related Art

The single major cause of death in potentially salvageable combat casualties is hemorrhage, and the greatest opportunity for reducing mortality and morbidity of battlefield casualties involves aggressive hemorrhage control modalities. In the management of combat casualties who are hemorrhaging, hypothermia prevention and management is of critical importance. Hypothermia can lead to cardiac arrhythmias, decreased cardiac output, increased systemic vascular resistance, and most importantly, induced coagulopathy by inhibition of the clotting cascade. If hypothermia is not prevented in this casualty demographic the potential exists that the injured person will not be able to form a clot due to the disruption of the clotting cascade and may potentially bleed to death from an otherwise survivable wounding.

The prior art discloses various means for treating and protecting against hypothermia including emergency blankets, insulated apparel, and heating devices, such as air activated heating pads. For example, U.S. Patent Publication No. 2005/0044602 discloses self-heating apparel having air activated heating elements sealed between layers of fabric and disposed throughout the apparel for providing a heating effect for the wearer. Another example is provided by U.S. Pat. No. 5,386,604, which discloses a patient rescue bag having top and bottom layers of insulated weatherproof material joined by releasable fasteners for adjusting the size of the bag to adapt to the size of the patient, while also keeping the patent warm and protected from the weather. Yet another example is provided by U.S. Pat. No. 4,998,296, which discloses a hypothermia protection suit having an integrated hood to be worn by a person in an emergency situation to provide extra warmth an protection from the weather.

When dealing with the rigors of combat and the treatment and prevention of hypothermia in wounded patients, the prior art devices do not provide a sufficient solution to the unique problems encountered by medics on the battlefield. For example, the current practice by medics on the battlefield treating a patient with hypothermia is to first wrap the patient is a blanket containing air activated heating elements. These blankets are not heat reflective or weatherproof and are susceptible to rips and tears, and thus have been difficult to use in the field due to their fragility. Next, the medic will wrap the patient in a weatherproof heat reflective blanket, typically one made of lightweight aluminized polyester commonly referred to as a space blanket, around the first heating blanket to reflect the patient's body heat and heat from the blanket back against the patient. Finally, the medical will apply a heat reflective cap to the patient's head. The individual application of each of these items takes an unnecessarily long time. Worse, however, is the fact that by wrapping the patient in the heat reflective blanket, the air activated heating blanket does not get a sufficient supply of oxygen to sustain an acceptable level of heating capacity for extended time periods. Additionally, once the patient is wrapped in the blankets, the medic cannot easily check on the patient's wounds without unwrapping the patient, which exposes the patient and reduces the heat buildup around the patent intended to manage or prevent hypothermia.

Accordingly, it is an object of the present invention to provide a single use lightweight durable hypothermia treatment device having a heat reflective body sack that will totally encapsulate the patient minus the face.

It is another object of the present invention to provide a hypothermia treatment sack containing self-activating heating pads directly exposed to air on the exterior of the sack that will warm once the sack is exposed to air, and which are also exposed on the interior side of the sack to provide direct heat over a wounded patient's body for an extended time period.

It is another object of the present invention to provide a hypothermia treatment sack that allows for quick access of the extremities and core of the patient from any location around the perimeter sides of the sack while minimizing patient exposure and protecting the patient from the weather.

It is another object of the present invention to provide a hypothermia treatment sack that is packaged in a vacuumed sealed rugged container for surviving the rigors of battlefield deployment.

SUMMARY OF THE INVENTION

The above objectives are accomplished according to the present invention by providing a hypothermia treatment sack for temporarily preventing and managing hypothermia, particularly in field conditions, as described below. The hypothermia treatment sack comprises a top sheet having a generally rectangular shape for covering a patient's body, and a bottom sheet having a corresponding rectangular shape to the top sheet for engaging the top sheet to form a patient receiving cavity between the top and bottom sheets. The top and bottom sheets each have a weatherproof exterior side for repelling wind and water from entering the patient receiving cavity, and a heat reflective interior side for preventing heat from escaping the patient receiving cavity. A plurality of self-activating heating pads are carried in the top sheet for producing heat when exposed to air. The heating pads have a first side exposed on the weatherproof exterior side of the top sheet for being in direct communication with air surrounding the top sheet to provide a generally unrestricted airflow to the heating pads, and a second side of the heating pads exposed on the heat reflective interior side of the top sheet for being in direct communication with the patient receiving cavity to radiate heat directly into the patient receiving cavity to warm a patient placed therein.

In a further embodiment, a plurality of the self-activating heating pads are spatially arranged about a torso section of the top sheet for radiating heat directly over a patient's torso when the patient is within the patient receiving cavity.

In a further advantageous embodiment, the torso section of the top sheet includes an upper torso area, a mid-torso area, and a lower torso area; and, wherein at least one of the self-activating heating pads is disposed in each of the upper torso area, the mid-torso area, and the lower torso area for radiated heat directly over a patient's entire torso. In a further embodiment, a first self-activating heating pad is carried on a left side of the upper torso area, and a second self-activating heating pad is carried on a right side of the upper torso area generally parallel with the first self-activating heating pad for radiating heat directly over the left and right sides of a patient's upper torso. In a further embodiment, a third self-activating heating pad is carried on a left side of the mid-torso area, and a forth self-activating heating pad is carried on a right side of the mid-torso area generally parallel with the third self-activating heating pad for radiating heat directly over the left and right sides of a patient's mid-torso. In a further embodiment, a fifth self-activating heating pad is carried on a left side of the lower torso area, and a sixth self-activating heating pad is carried on a right side of the lower torso area generally parallel with the fifth self-activating heating pad for radiating heat directly over the left and right sides of a patient's lower torso.

In a further advantageous embodiment, a plurality of the self-activating heating pads are spatially arranged about a lower extremity section of the top sheet for radiating heat directly over a patient's lower extremities when the patient is within the patient receiving cavity.

In another advantageous embodiment, a hood is carried by the bottom sheet for covering a patient's head when placed in the patient receiving cavity. Further, at least one self-activating heating pad may be carried by the hood for radiating heat over a patient's head. In a further embodiment, the hood includes a weatherproof exterior side for repelling wind and water from a patient's head, and a heat reflective interior side for preventing heat from escaping through the hood. Preferably, the heating pad carried by the hood includes a first side exposed on the weatherproof exterior side of the hood for being in direct communication with air surrounding the hood to provide a generally unrestricted airflow to the heating pad in the hood, and a second side of the heating pad in the hood exposed on the heat reflective interior side of the hood for radiating heat directly over the patient's head.

In a further advantageous embodiment, a neck closure is carried by the hood adapted for surrounding a patient's neck. Preferably, the neck closure includes a weatherproof exterior side for repelling wind and water from the patient's neck, and a heat reflective interior side for reducing heat loss from the patient's neck.

In a further advantageous embodiment, a clear chart pocket is carried on the weatherproof exterior side of the top sheet for holding papers and allowing the papers to be viewed without being removed from the chart pocket.

In a further advantageous embodiment, the self-activating heating pads include a flange affixed to the top sheet for securing the heating pads within the top sheet.

In a further advantageous embodiment, the top sheet and the bottom sheet comprise aluminized polyester for repelling wind and water and reflecting heat.

In a further advantageous embodiment, the weatherproof exterior side of the top and bottom sheets is a generally dark green color for camouflaging injured patient's on a battlefield.

In a further advantageous embodiment, releasable connectors are carried along a perimeter portion of the top and bottom sheets for releasably connecting the top and bottom sheets while allowing patient access from any location around the perimeter of the sheets when connected together. Preferably, the releasable connectors comprise cooperating hook and loop fasteners arranged in strips extending continuously along a left perimeter side, a bottom perimeter side and a right perimeter side of the top and bottom sheets; and, wherein the strips of hook and loop fasteners are discontinuous along a top perimeter side of the top and bottom sheets for providing a neck opening between the top and bottom sheets when connected together.

In a further advantageous embodiment, a plurality of self-activating heating pads are carried in the bottom sheet for producing heat when exposed to air, wherein the heating pads in the bottom sheet have a first side exposed on the weatherproof exterior side of the bottom sheet for being in direct communication with air surrounding the bottom sheet to provide a generally unrestricted airflow to the heating pads in the bottom sheet, and a second side of the heating pads in the bottom sheet exposed on the heat reflective interior side of the bottom sheet for being in direct communication with the patient receiving cavity to radiate heat directly into the patient receiving cavity to warm a patient placed therein.

In another embodiment, the invention includes a packaged single use hypothermia treatment sack comprising a treatment sack having a top sheet and a bottom sheet releasably connecting around a perimeter portion of the sheets to form a patient receiving cavity while allowing for patient access from any location along the perimeter of the sheets when connected together; a plurality of self-activating heating pads carried by the top sheet for producing heat when exposed to air and radiating the heat directly into the patient receiving cavity; a vacuum sealed pliable container maintaining a high gas barrier while sealed; and, the treatment sack being packaged within the container substantially free of air to prevent activation of the self-activating heating pads until the vacuum sealed pliable container is opened.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein.

DETAILED DESCRIPTION OF A PREFERRED EMBODIMENT

Figure 1:
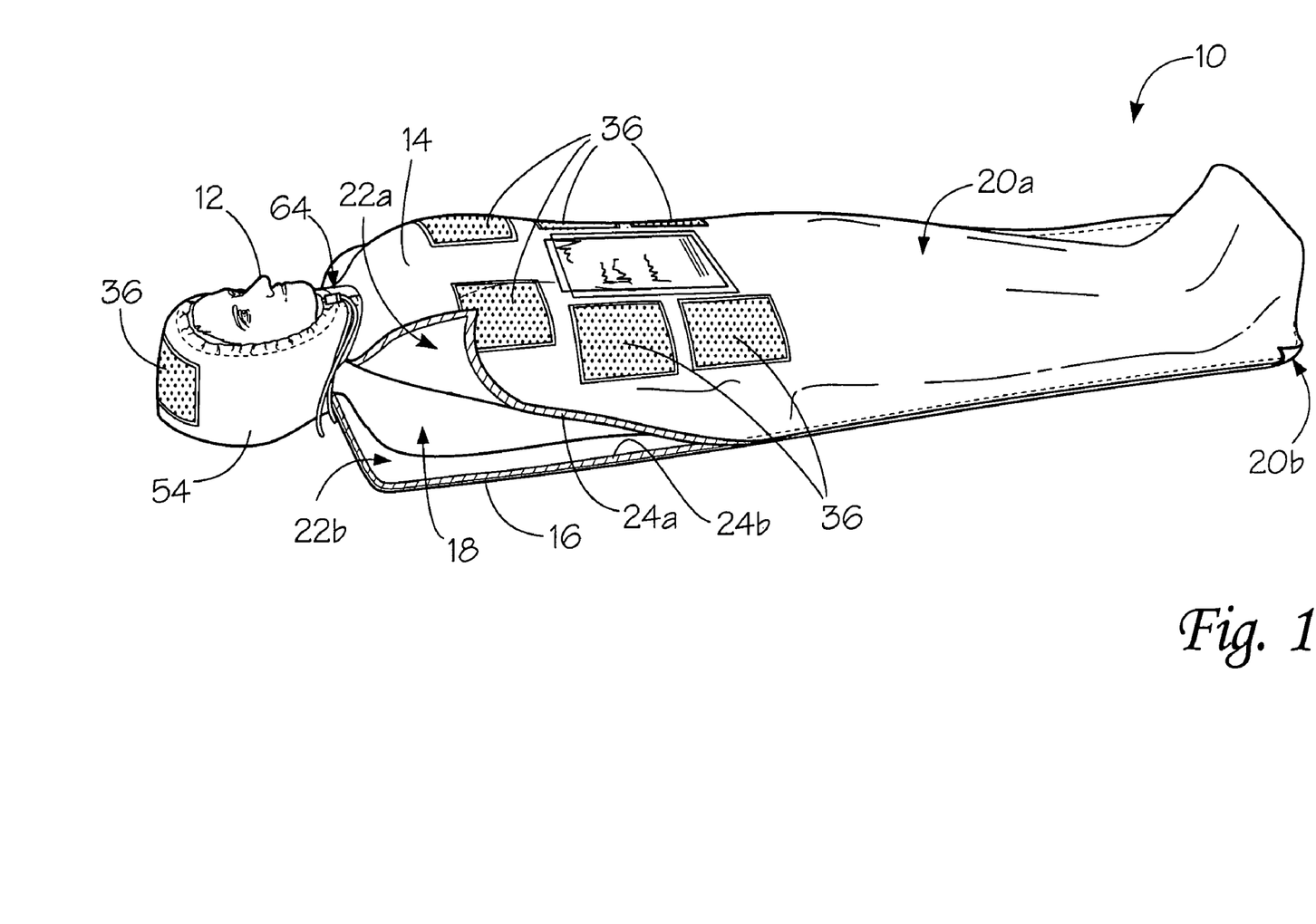
FIG. 1 shows a perspective view of a patient in a hypothermia treatment sack according to the present invention.

With reference to the drawings, the invention will now be described in more detail. Referring to FIG. 1, a hypothermia treatment sack, designated generally as 10, is shown surrounding a patient 12 for temporarily preventing and managing hypothermia. The hypothermia treatment sack disclosed herein is a durable cost efficient first aid device designed particularly for single use applications in the field by first responders to treat conditions associated with hypothermia by warming the patient and protecting the patient from inclement weather conditions until the patient can be transported the appropriate treatment facility.

The hypothermia treatment sack 10 includes a top sheet 14 having a generally rectangular shape of sufficient proportions for covering a patient's body. The hypothermia treatment sack 10 also includes a bottom sheet 16 having a corresponding rectangular shape to top sheet 14 for engaging the top sheet to form a patient receiving cavity, designated generally as 18, between top sheet 14 and bottom sheet 16. Top sheet 14 and bottom sheet 16 each have a weatherproof exterior side, designated generally as 20a and 20b, respectively, for repelling wind and water from entering patient receiving cavity 18. Further, top sheet 14 and bottom sheet 16 each have a heat reflective interior side, designated generally as 22a and 22b, respectively, for preventing heat from escaping patient receiving cavity 18. In a preferred embodiment, top sheet 14 and bottom sheet 16 comprise aluminized polyester which is capable of both repelling wind and water and reflecting heat. In this arrangement, only one sheet of materials is required to form each of top sheet 14 and bottom sheet 16, which reduces bulk and weight for storage and transport in the field. Further, aluminized polyester is extremely durable and well suited to the rigors of extreme field conditions, such on a battlefield.

In a further advantageous embodiment, weatherproof exterior sides 20a and 20b of top and bottom sheets 14 and 16, respectively, are a generally dark green color, such as olive drab, for camouflaging injured patient's on a battlefield. In order to reduce manufacturing costs, heat reflective interior sides 22a and 22b may be the standard reflective finish common to aluminized polyester, which can be used to attract attention of rescuers if required.

Figures 2A, 2B:
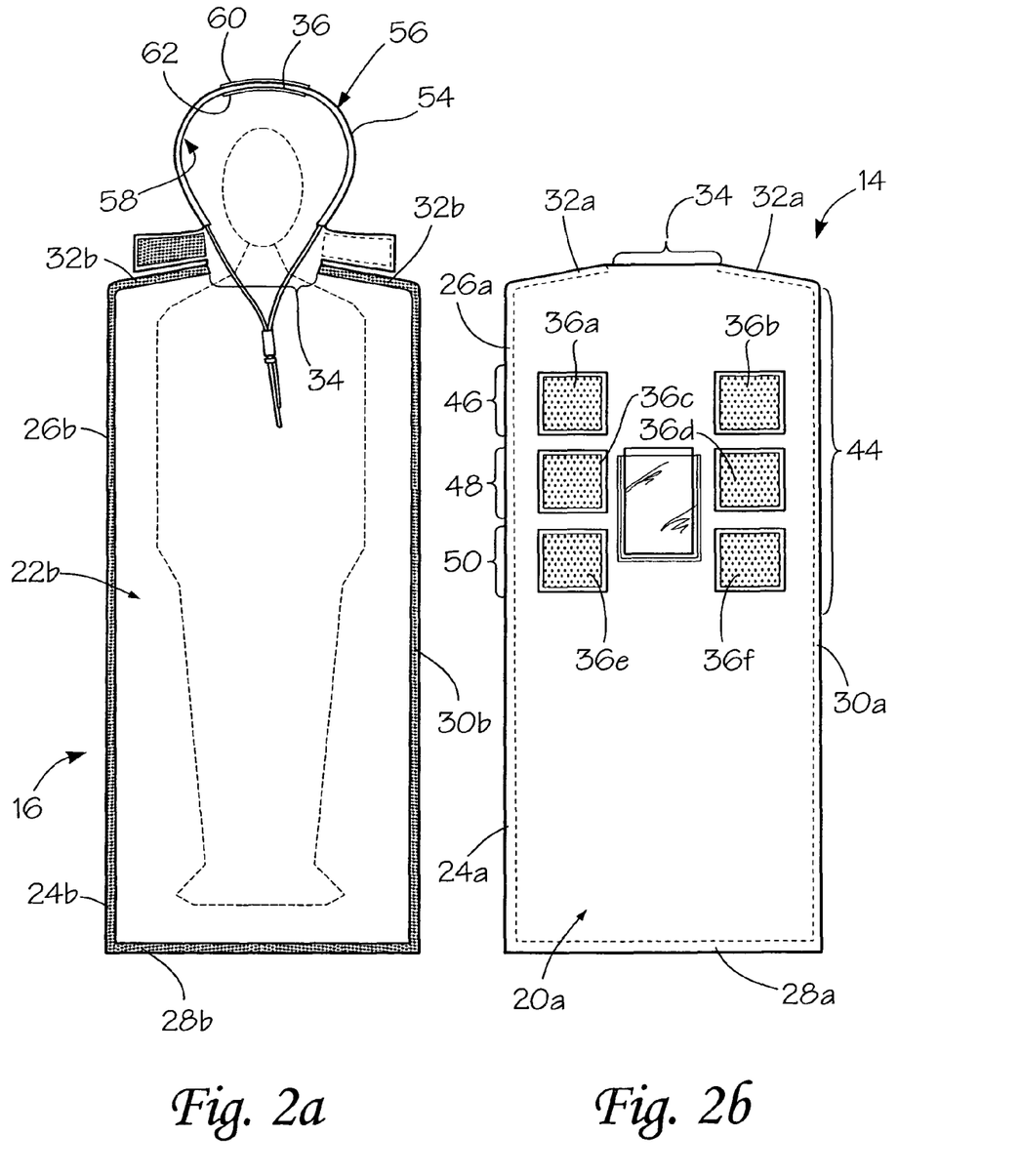
FIG. 2a shows a top down view of an interior side of a bottom sheet of the sack according to the present invention.
FIG. 2b shows a top down view of an exterior side of a top sheet of the sack according to the present invention.

Referring to FIG. 1, to combine top sheet 14 with bottom sheet 16 to form patient receiving cavity 18, releasable connectors 24a and 24b are carried along a perimeter portion of top sheet 14 and bottom sheet 16 for releasably connecting the top and bottom sheets. This provides patient access from any location around the perimeter of the sheets when connected together. In a preferably embodiment, releasable connectors 24a and 24b comprise cooperating hook and loop fasteners, such as Velcro®. Referring to FIGS. 2a and 2b, releasable connectors 24a and 24b are arranged into strips 26a and 26b extending continuously along a left perimeter side, strips 28a and 28b extending continuously along a bottom perimeter side, and strips 30a and 30b extending continuously along a right perimeter side 30 of top sheet 14 and bottom sheet 16. Strips of hook and loop fasteners 32a and 32b are arranged in a discontinuous manner along a top perimeter side of top sheet 14 and bottom sheet 16 for providing a neck opening, designated generally as 34, between the top and bottom sheets when connected together.

Figure 4:
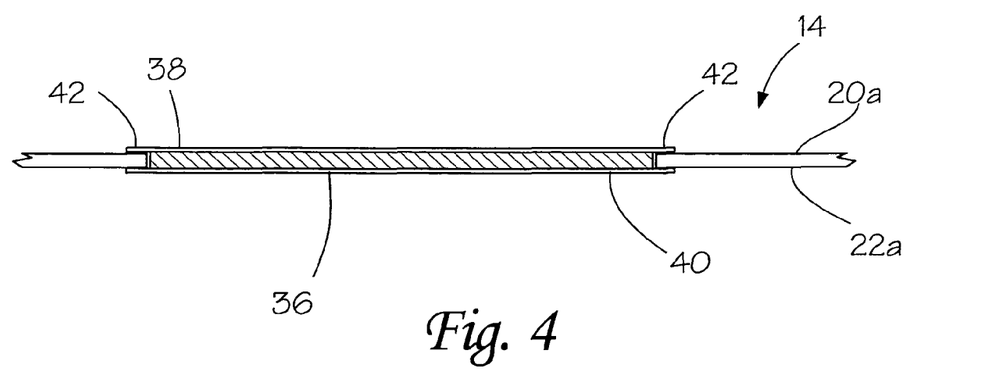
FIG. 4 shows a cross section view of a portion of the top sheet carrying a self-activating heating pad according to the present invention; and, FIG. 5 shows a perspective view of the sack packaged in a vacuum sealed container according to the present invention.

Referring to FIG. 1, a plurality of self-activating heating pads 36 are carried in top sheet 14 for producing heat when exposed to air. Self-activating heating pads 36 are well known in the prior art and consist essentially of various combinations of iron powder, water, salt, and activated carbon which produces an exothermal reaction when exposed to oxygen. Referring to FIG. 4, heating pads 36 have a first side 38 exposed on weatherproof exterior side 20a of top sheet 14 for being in direct communication with air surrounding top sheet 14 to provide a generally unrestricted airflow to heating pads 36. A second side 40 of heating pads 36 are exposed on heat reflective interior side 22a of top sheet 14 for being in direct communication with patient receiving cavity 18 to radiate heat directly into the patient receiving cavity to warm a patient placed therein. This avoids the serious problem with the prior art that restricts airflow to the heating pads which causes reduced heat and reduced heating time from the heating pads. In a preferred embodiment, the size and shape of heating pads 36 should be sufficient to maintain a temperature of 106° within patient receiving cavity 18 for a period of approximately 8 hours.

Referring to FIG. 4, in a preferred embodiment, self-activating heating pads 36 include a flange 42 affixed to the top sheet for securing the heating pads within the top sheet. Heating pads may also be carried by bottom sheet 16 in the same manner as described above and shown in FIG. 4.

Referring to FIG. 2b, in a preferred embodiment, a plurality of the self-activating heating pads 36 are spatially arranged about a torso section, designated generally as 44, of top sheet 14 for radiating heat directly over a patient's torso when the patient is within patient receiving cavity 18. More particularly, in a further advantageous embodiment, torso section 44 of top sheet 14 includes an upper torso area 46, a mid-torso area 48, and a lower torso area 50. At least one of self-activating heating pads 36 is disposed in each of upper torso area 46, mid-torso area 48, and lower torso area 50 for radiated heat directly over a patient's entire torso. Preferably, a first self-activating heating pad 36a is carried on a left side of the upper torso area 46, and a second self-activating heating pad 36b is carried on a right side of the upper torso area 46 generally parallel with first self-activating heating pad 36a for radiating heat directly over the left and right sides of a patient's upper torso. Additionally, a third self-activating heating pad 36c is carried on a left side of mid-torso area 48, and a forth self-activating heating pad 36d is carried on a right side of mid-torso area 48 generally parallel with third self-activating heating pad 36c for radiating heat directly over the left and right sides of a patient's mid-torso. Further, it is preferred that a fifth self-activating heating pad 36e is carried on a left side of lower torso area 50, and a sixth self-activating heating pad 36f is carried on a right side of lower torso area 50 generally parallel with fifth self-activating heating pad 36e for radiating heat directly over the left and right sides of a patient's lower torso.

Figures 3A, 3B:
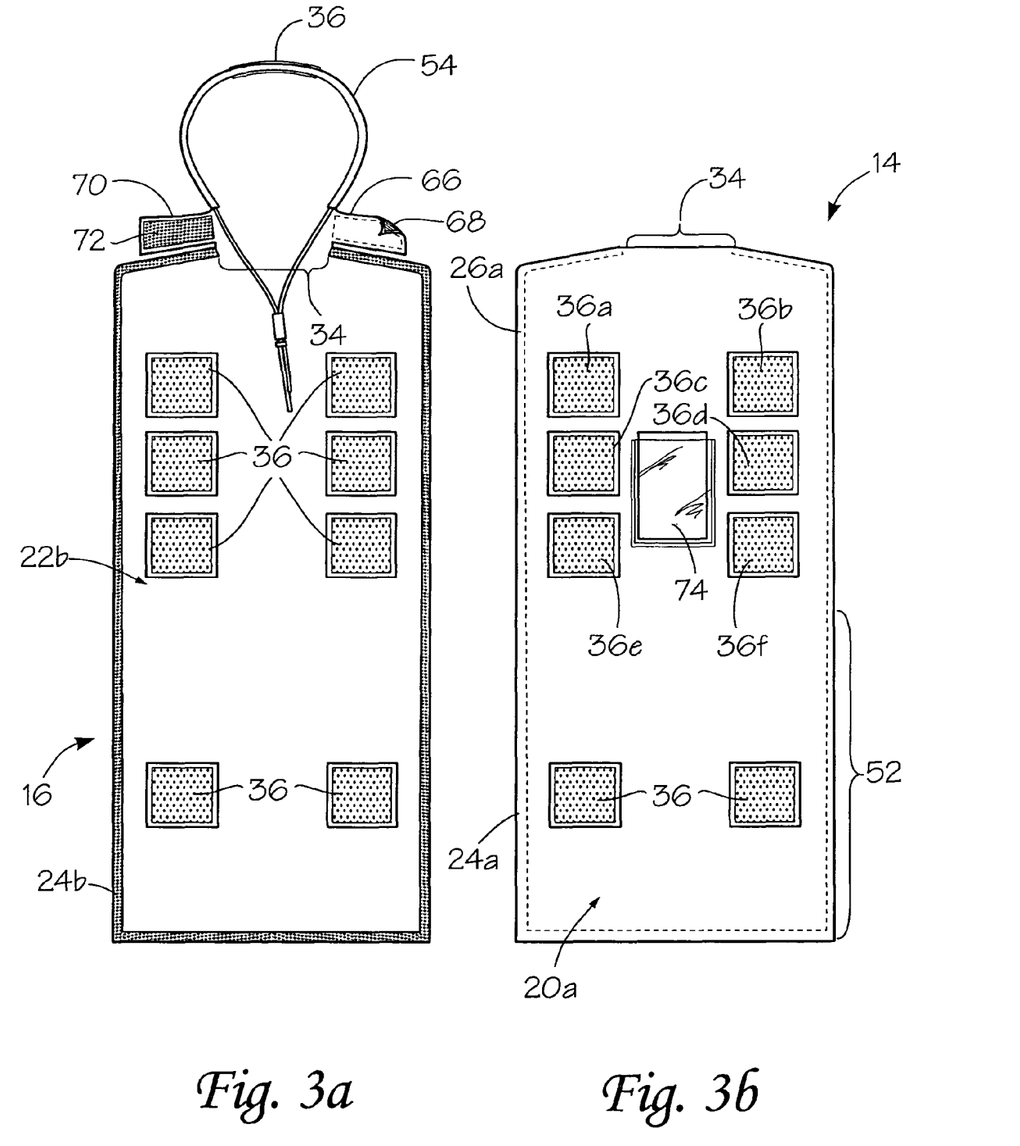
FIG. 3a shows a top down view of an alternative embodiment of the bottom sheet according to the present invention.
FIG. 3b shows a top down view of an alternative embodiment of the top sheet according to the present invention.

Referring to FIG. 3b, in a further advantageous embodiment, a plurality of the self-activating heating pads 36 are spatially arranged about a lower extremity section 52 of top sheet 14 for radiating heat directly over a patient's lower extremities when the patient is within the patient receiving cavity. The number and arrangement of heating pads 36 in torso section 44 and lower extremity section 52 can be varied without departing from the spirit and scope of the present invention, and the illustrated embodiment is provided by way of example only.

Referring to FIG. 3a, in a further advantageous embodiment, a plurality of self-activating heating pads 36 may be carried in bottom sheet 16 in the same manner and arrangement as discussed above for top sheet 14 for producing heat when exposed to air. As with heating pads 36 carried by top sheet 14 shown in FIG. 4, heating pads 36 in bottom sheet 16 have a first side exposed on weatherproof exterior side 20b (FIG. 1) of bottom sheet 16 for being in direct communication with air surrounding bottom sheet 16 to provide a generally unrestricted airflow to the heating pads in the bottom sheet. Further, a second side of heating pads 36 in bottom sheet 16 are exposed on heat reflective interior side 22b of bottom sheet for being in direct communication with patient receiving cavity 18 to radiate heat directly into the patient receiving cavity to warm a patient placed therein.

Referring to FIGS. 1 and 2a, in further preferred embodiment, a hood 54 is carried by bottom sheet 16 for covering a patient's head when placed in the patient receiving cavity. Preferably, at least one self-activating heating pad 36 may be carried by the hood for radiating heat over a patient's head. In a further embodiment, hood 54 includes a weatherproof exterior side, designated generally as 56 for repelling wind and water from a patient's head. Further, hood 54 includes a heat reflective interior side 58 for preventing heat from escaping through the hood. As with top sheet 14 and bottom sheet 16, hood 54 may be constructed from aluminized polyester to provide lightweight durable wind and water resistance while also providing heat reflective capability. Preferably, the heating pad 36 carried by hood 54 includes a first side 60 exposed on weatherproof exterior side 56 of hood 54 for being in direct communication with air surrounding the hood to provide a generally unrestricted airflow to the heating pad in the hood, and a second side of heating pad 36 in hood 54 is exposed on heat reflective interior side 58 of hood 54 for radiating heat directly over the patient's head.

Referring to FIGS. 1 and 3a, in a preferred embodiment, a neck closure, designated generally as 64, is carried by 54 and adapted for surrounding a patient's neck. Preferably, the neck closure includes a weatherproof exterior side for repelling wind and water from the patient's neck, and a heat reflective interior side for reducing heat loss from the patient's neck. Neck closure 64 includes a first flap 66 including a first portion of hook and loop fastener 68, and a second flap 70 including a second portion of cooperating hook and loop fastener 72 for engaging hook and loop fastener 68 of first flap 66, wherein first flap 66 and second flap 70 overlap each other around a patient's neck.

Referring to FIGS. 1 and 3b, a further advantageous embodiment, a clear chart pocket 74 is carried on weatherproof exterior side 20a of top sheet 14 for holding papers and allowing the papers to be viewed without being removed from the chart pocket.

Figure 5:
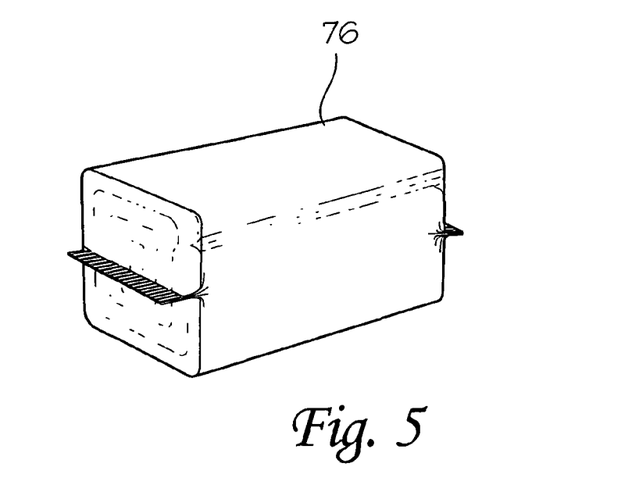

Referring to FIG. 5, hypothermia treatment sack 10 is packaged within a vacuum sealed pliable container 76 capable of maintaining a high gas barrier while sealed. The treatment sack must be packaged within the container substantially free of air to prevent activation of the self-activating heating pads until the vacuum sealed pliable container is opened.

While a preferred embodiment of the invention has been described using specific terms, such description is for illustrative purposes only, and it is to be understood that changes and variations may be made without departing from the spirit or scope of the following claims.

What is claimed is:

1. A hypothermia treatment sack for temporarily preventing and managing hypothermia in field conditions, comprising:
   a top sheet having a generally rectangular shape for covering a patient's body;
   a bottom sheet having a corresponding rectangular shape to said top sheet for engaging said top sheet to form a patient receiving cavity between said top and bottom sheets;
   said top and bottom sheets each having a weatherproof exterior side for repelling wind and water from entering said patient receiving cavity, and a heat reflective interior side for preventing heat from escaping said patient receiving cavity; and,
   a plurality of self-activating heating pads carried in said top sheet for producing heat when exposed to air, wherein said heating pads have a first side exposed on said weatherproof exterior side of said top sheet for being in direct communication with air surrounding said top sheet to provide a generally unrestricted airflow to said heating pads, and a second side of said heating pads exposed on said heat reflective interior side of said top sheet for being in direct communication with said patient receiving cavity to radiate heat directly into said patient receiving cavity to warm a patient placed therein.

2. The hypothermia treatment sack of claim 1 including a plurality of said self-activating heating pads spatially arranged about a torso section of said top sheet for radiating heat directly over a patient's torso when the patient is within said patient receiving cavity.

3. The hypothermia treatment sack of claim 2 wherein said torso section of said top sheet includes an upper torso area, a mid-torso area, and a lower torso area; and, wherein at least one of said self-activating heating pads is disposed in each of said upper torso area, said mid-torso area, and said lower torso area for radiated heat directly over a patient's entire torso.

4. The hypothermia treatment sack of claim 3 including a first self-activating heating pad carried on a left side of said upper torso area, and a second self-activating heating pad carried on a right side of said upper torso area generally parallel with said first self-activating heating pad for radiating heat directly over the left and right sides of a patient's upper torso.

5. The hypothermia treatment sack of claim 4 including a third self-activating heating pad carried on a left side of said mid-torso area, and a forth self-activating heating pad carried on a right side of said mid-torso area generally parallel with said third self-activating heating pad for radiating heat directly over the left and right sides of a patient's mid-torso.

6. The hypothermia treatment sack of claim 5 including a fifth self-activating heating pad carried on a left side of said lower torso area, and a sixth self-activating heating pad carried on a right side of said lower torso area generally parallel with said fifth self-activating heating pad for radiating heat directly over the left and right sides of a patient's lower torso.

7. The hypothermia treatment sack of claim 2 including a plurality of said self-activating heating pads spatially arranged about a lower extremity section of said top sheet for radiating heat directly over a patient's lower extremities when the patient is within said patient receiving cavity.

8. The hypothermia treatment sack of claim 1 including a hood carried by said bottom sheet for covering a patient's head when placed in said patient receiving cavity.

9. The hypothermia treatment sack of claim 8 including at least one self-activating heating pad carried by said hood for radiating heat over a patient's head.

10. The hypothermia treatment sack of claim 9 wherein said hood includes a weatherproof exterior side for repelling wind and water from a patient's head, and a heat reflective interior side for preventing heat from escaping through said hood.

11. The hypothermia treatment sack of claim 10 wherein said heating pad carried by said hood includes a first side exposed on said weatherproof exterior side of said hood for being in direct communication with air surrounding said hood to provide a generally unrestricted airflow to said heating pad in said hood, and a second side of said heating pad in said hood exposed on said heat reflective interior side of said hood for radiating heat directly over said patient's head.

12. The hypothermia treatment sack of claim 8 including a neck closure carried by said hood adapted for surrounding a patient's neck; and, wherein said neck closure includes a weatherproof exterior side for repelling wind and water from the patient's neck, and a heat reflective interior side for reducing heat loss from the patient's neck.

13. The hypothermia treatment sack of claim 1 including a clear chart pocket carried on said weatherproof exterior side of said top sheet for holding papers and allowing the papers to be viewed without being removed from said chart pocket.

14. The hypothermia treatment sack of claim 1 wherein said self-activating heating pads include a flange affixed to said top sheet for securing said heating pads within said top sheet.

15. The hypothermia treatment sack of claim 1 wherein said top sheet and said bottom sheet comprise aluminized polyester for repelling wind and water and reflecting heat.

16. The hypothermia treatment sack of claim 1 wherein said weatherproof exterior side of said top and bottom sheets is a generally dark green color for camouflaging injured patient's on a battlefield.

17. The hypothermia treatment sack of claim 1 including releasable connectors carried along a perimeter portion of said top and bottom sheets for releasably connecting said top and bottom sheets while allowing patient access from any location around the perimeter of said sheets when connected together.

18. The hypothermia treatment sack of claim 17 wherein said releasable connectors comprise cooperating hook and loop fasteners arranged in strips extending continuously along a left perimeter side, a bottom perimeter side and a right perimeter side of said top and bottom sheets; and, wherein said strips of hook and loop fasteners are discontinuous along a top perimeter side of said top and bottom sheets for providing a neck opening between said top and bottom sheets when connected together.

19. The hypothermia treatment sack of claim 1 including a plurality of self-activating heating pads carried in said bottom sheet for producing heat when exposed to air, wherein said heating pads in said bottom sheet have a first side exposed on said weatherproof exterior side of said bottom sheet for being in direct communication with air surrounding said bottom sheet to provide a generally unrestricted airflow to said heating pads in said bottom sheet, and a second side of said heating pads in said bottom sheet exposed on said heat reflective interior side of said bottom sheet for being in direct communication with said patient receiving cavity to radiate heat directly into said patient receiving cavity to warm a patient placed therein.

20. A packaged single use hypothermia treatment sack comprising:
a treatment sack having a top sheet and a bottom sheet releasably connecting around a perimeter portion of said sheets to form a patient receiving cavity while allowing for patient access from any location along the perimeter of said sheets when connected together;
a plurality of self-activating heating pads carried by said top sheet for producing heat when exposed to air and radiating the heat directly into said patient receiving cavity;
a vacuum sealed pliable container maintaining a high gas barrier while sealed; and,
said treatment sack being packaged within said container substantially free of air to prevent activation of said self-activating heating pads until said vacuum sealed pliable container is opened.

21. The packaged hypothermia treatment sack of claim 20 wherein said top and bottom sheets each having an exterior side constructed from a weatherproof material for repelling wind and water from entering said patient receiving cavity, and an interior side constructed from a heat reflective material for preventing heat from escaping said patient receiving cavity.

22. The packaged hypothermia treatment sack of claim 21 wherein said self-activating heating pads have a first side exposed on said exterior side of said top sheet for being in direct communication with air surrounding said top sheet to provide a generally unrestricted airflow to said heating pads, and a second side of said heating pads exposed on said interior side of said top sheet for being in direct communication with said patient receiving cavity to radiate heat directly into said patient receiving cavity to warm a patient placed therein.

23. The packaged hypothermia treatment sack of claim 22 including a hood carried by said bottom sheet for covering a patient's head when placed in said patient receiving cavity; and, wherein at least one of said self-activating heating pads is carried by said hood having a first side exposed on an exterior side of said hood for being in direct communication with air surrounding said hood to provide a generally unrestricted airflow to said heating pad in said hood, and a second side of said heating pad in said hood exposed on an interior side of said hood for radiating heat directly over said patient's head.

24. The packaged hypothermia treatment sack of claim 23 including a neck closure carried by said hood adapted for surrounding a patient's neck; and, wherein said neck closure includes a weatherproof exterior side for repelling wind and water from the patient's neck, and a heat reflective interior side for reducing heat loss from the patient's neck.

25. The packaged hypothermia treatment sack of claim 24 including a clear chart pocket carried on said exterior side of said top sheet for holding papers and allowing the papers to be viewed without being removed from said chart pocket.

26. The packaged hypothermia treatment sack of claim 25 wherein said top sheet, said bottom sheet, said hood, and said neck closure comprise aluminized polyester for repelling wind and water and reflecting heat.

27. The packaged hypothermia treatment sack of claim 26 wherein mean for releasably connecting said top and bottom sheets comprise cooperating hook and loop fasteners arranged in strips extending continuously along a left perimeter side, a bottom perimeter side and a right perimeter side of said top and bottom sheets; and, wherein said strips of hook and loop fasteners are discontinuous along a top perimeter side of said top and bottom sheets for providing a neck opening between said top and bottom sheets when connected together.

28. The packaged hypothermia treatment sack of claim 27 including a plurality of self-activating heating pads carried in said bottom sheet for producing heat when exposed to air, wherein said heating pads in said bottom sheet have a first side exposed on said exterior side of said bottom sheet for being in direct communication with air surrounding said bottom sheet to provide a generally unrestricted airflow to said heating pads in said bottom sheet, and a second side of said heating pads in said bottom sheet exposed on said interior side of said bottom sheet for being in direct communication with said patient receiving cavity to radiate heat directly into said patient receiving cavity to warm a patient placed therein.

29. A hypothermia treatment sack for temporarily preventing and managing hypothermia in field conditions, comprising:
a top sheet having a plurality of self-activating heating pads for producing heat when exposed to air;
a bottom sheet having a corresponding shape to said top sheet for releasably connecting with said top sheet generally along the perimeter of said top and bottom sheets to form a patient receiving cavity between said top and bottom sheets to be heated by said self-activating heating pads and providing patient access from any location around the perimeter of said sheets;
a plurality of said releasable connectors extending continuously along a left perimeter side, a bottom perimeter side and a right perimeter side of said top and bottom sheets for completely sealing the perimeter of said top sheet to said bottom sheet on said left, right and bottom perimeter sides; and, wherein said releasable connectors extend discontinuously along a top perimeter side of said top and bottom sheets for providing a neck opening between said top and bottom sheets when connected together; and, a hood carried by said bottom sheet adjacent said neck opening for covering a patient's head when placed in said patient receiving cavity, wherein at least one self-activating heating pad carried by said hood.

30. The hypothermia treatment sack of claim 29 wherein said top and bottom sheets each have a weatherproof exterior side for repelling wind and water from entering said patient receiving cavity, and a heat reflective interior side for preventing heat from escaping said patient receiving cavity.

31. The hypothermia treatment sack of claim 30 wherein said self-activating heating pads have a first side exposed on said weatherproof exterior side of said top sheet for being in direct communication with air surrounding said top sheet to provide a generally unrestricted airflow to said heating pads, and a second side of said heating pads exposed on said heat reflective interior side of said top sheet for being in direct communication with said patient receiving cavity to radiate heat directly into said patient receiving cavity to warm a patient placed therein.

32. The hypothermia treatment sack of claim 30 including a plurality of self-activating heating pads carried in said bottom sheet for producing heat when exposed to air, wherein said heating pads in said bottom sheet have a first side exposed on said weatherproof exterior side of said bottom sheet for being in direct communication with air surrounding said bottom sheet to provide a generally unrestricted airflow to said heating pads in said bottom sheet, and a second side of said heating pads in said bottom sheet exposed on said heat reflective interior side of said bottom sheet for being in direct communication with said patient receiving cavity to radiate heat directly into said patient receiving cavity to warm a patient placed therein.

33. The hypothermia treatment sack of claim 29 wherein said hood includes a weatherproof exterior side for repelling wind and water from a patient's head, and a heat reflective interior side for preventing heat from escaping through said hood.

34. The hypothermia treatment sack of claim 33 wherein said heating pad carried by said hood includes a first side exposed on said weatherproof exterior side of said hood for being in direct communication with air surrounding said hood to provide a generally unrestricted airflow to said heating pad in said hood, and a second side of said heating pad in said hood exposed on said heat reflective interior side of said hood for radiating heat directly over said patient's head.

35. The hypothermia treatment sack of claim 29 including a neck closure carried by said hood adapted for surrounding a patient's neck; and, wherein said neck closure includes a weatherproof exterior side for repelling wind and water from the patient's neck, and a heat reflective interior side for reducing heat loss from the patient's neck.

36. The hypothermia treatment sack of claim 29 including a clear chart pocket carried on said weatherproof exterior side of said top sheet for holding papers and allowing the papers to be viewed without being removed from said chart pocket.

37. The hypothermia treatment sack of claim 29 wherein said top sheet, said bottom sheet and said hood comprise aluminized polyester for repelling wind and water and reflecting heat.

* * * * *